(12) United States Patent
Knepper et al.

(10) Patent No.: US 11,547,829 B2
(45) Date of Patent: Jan. 10, 2023

(54) HEATED CONDUIT FOR DELIVERING GAS TO A PATIENT

(71) Applicant: KONINKLIJKE PHILIPS N.V., Eindhoven (NL)

(72) Inventors: Michael B Knepper, Friedens, PA (US); Lawrence Anthony Jacob, Sewickley, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 451 days.

(21) Appl. No.: 16/717,477

(22) Filed: Dec. 17, 2019

(65) Prior Publication Data

US 2020/0206442 A1    Jul. 2, 2020

Related U.S. Application Data

(60) Provisional application No. 62/787,556, filed on Jan. 2, 2019.

(51) Int. Cl.
| | | |
|---|---|---|
| *A61M 16/10* | (2006.01) | |
| *A61M 16/00* | (2006.01) | |
| *A61M 16/06* | (2006.01) | |
| *A61M 16/08* | (2006.01) | |

(52) U.S. Cl.
CPC ...... *A61M 16/1095* (2014.02); *A61M 16/022* (2017.08); *A61M 16/0616* (2014.02); *A61M 16/0875* (2013.01); *A61M 16/0066* (2013.01); *A61M 2016/0024* (2013.01); *A61M 2016/0039* (2013.01); *A61M 2205/3368* (2013.01); *A61M 2205/3673* (2013.01); *A61M 2205/50* (2013.01)

(58) Field of Classification Search
CPC .............. A61M 16/08; A61M 16/0816; A61M 16/0875; A61M 16/1095
See application file for complete search history.

(56) References Cited

U.S. PATENT DOCUMENTS

| | | | |
|---|---|---|---|
| 2002/0083947 A1* | 7/2002 | Seakins ............... | H02H 1/0015 128/204.17 |
| 2011/0023874 A1* | 2/2011 | Bath ................. | A61M 16/0816 128/203.14 |
| 2015/0101600 A1* | 4/2015 | Miller .................. | A61M 16/06 128/203.14 |
| 2016/0354573 A1* | 12/2016 | Buswell ............ | A61M 16/1095 |
| 2018/0200470 A1* | 7/2018 | Dixon ............... | A61M 16/0875 |
| 2018/0280651 A1* | 10/2018 | Liu ..................... | A61M 16/026 |
| 2019/0275281 A1* | 9/2019 | Creusot ............ | A61M 16/0875 |

* cited by examiner

*Primary Examiner* — Joseph D. Boecker
(74) *Attorney, Agent, or Firm* — Michael W. Haas (57) ABSTRACT

A conduit for communicating a flow of breathing gas from a pressure generating device to the airway of a patient. The conduit includes a first end which is structured to be coupled to the pressure generating device for receiving the flow of breathing gas and an opposite second end which is structured to be coupled to a patient interface device. The conduit further includes an active control element positioned at or near the second end; a first heating wire connected between the active control element and a first connection terminal positioned at or about the first end; and a second heating wire connected between the active control element and a second connection terminal positioned at or about the first end. Each of the first and second connection terminals are structured to be connected to a tube power supply.

16 Claims, 6 Drawing Sheets

HEATED CONDUIT FOR DELIVERING GAS TO A PATIENT

CROSS-REFERENCE TO RELATED APPLICATIONS

This patent application claims the priority benefit under 35 U.S.C. § 119(e) of U.S. Provisional Application Nos. 62/784,565 and 62/787,556, filed on Dec. 24, 2018 and Jan. 2, 2019, respectively, the contents of each of which are herein incorporated by reference.

BACKGROUND OF THE INVENTION

1. Field of the Invention

The present invention relates to heated conduits for communicating a flow of breathing gas from a pressure generating device to the airway of a patient. The present invention also relates to airway pressure support systems including heated conduits for delivering a flow of breathing gas to an airway of a patient.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory airflow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory airflow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

"Rainout" is a condition that occurs when the humidity of the air within the air flow path of a pressure support system (e.g. the CPAP unit, hose, and mask) condenses on the inside surfaces of the components of the air flow path, resulting in pooling of water within the airflow path over time (which is a nuisance to the patient receiving therapy). When rainout occurs, it often disturbs the patient, which in turn may cause the patient to discontinue therapy for the remainder of the night. Rainout occurs because the air within the airflow path is heated and humidified by the pressure support device (or the patient's own body in the case of exhaled air), but the temperatures of the walls of the airflow circuit (e.g. a hose or mask) are equilibrated with the ambient environment which may be significantly cooler than the air in the airflow circuit. The temperature of the air within the airflow circuit decreases when it makes contact with the walls of the circuit, resulting in condensation (i.e., "rainout").

Figure 1:
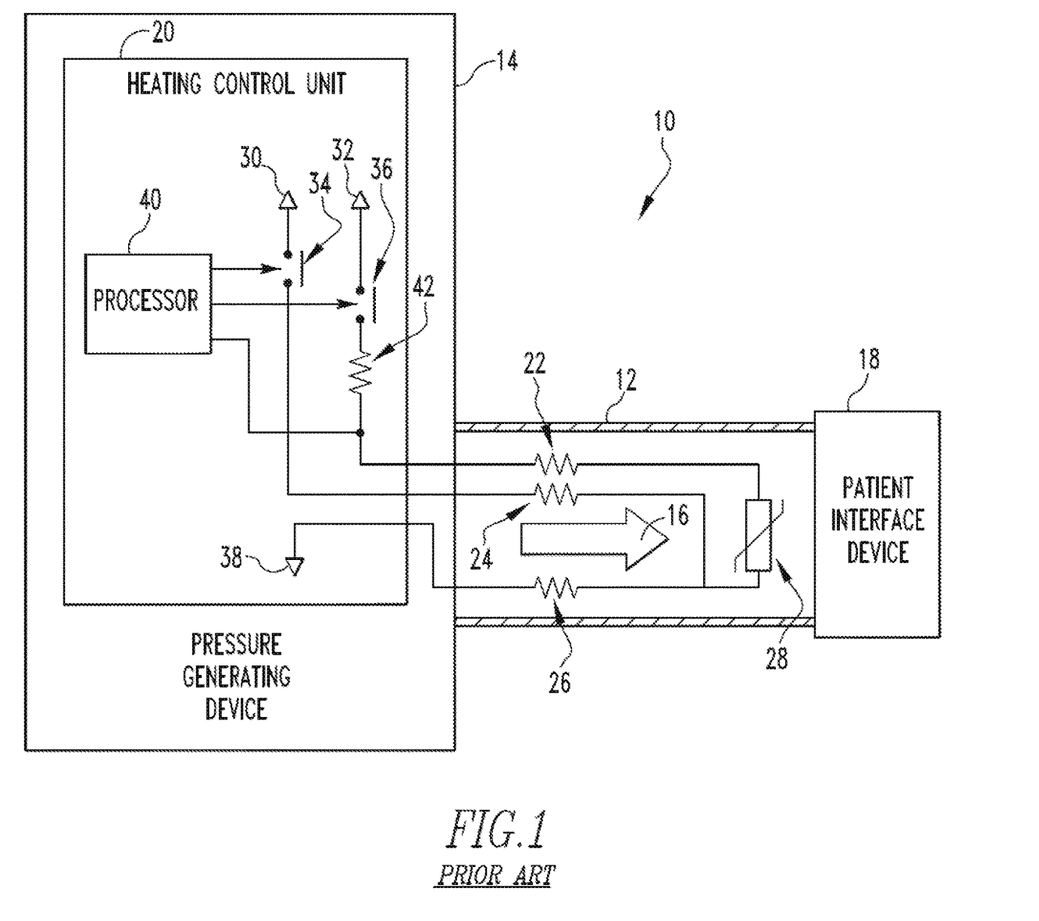
FIG. 1 is a schematic diagram showing an airway pressure support system with a heated conduit.

Some pressure support systems attempt to reduce rainout by adding heating elements to the walls of the airflow circuit (e.g. a heated conduit). Typical heated wire breathing circuits are 3 or 4 wire configurations with separate heater wire and temperature sensor circuits. The temperature sensor is mounted proximal to the patient to monitor the air temperature during therapy and provide a closed loop control function to maintain the desired airpath temperature. An example of such a system is shown in FIG. 1 which shows an example of a pressure support system 10 with heating in its conduit 12. Pressure support system 10 includes a base unit 14 including a pressure generating device that generates airflow, shown generally by arrow 16, that is provided to a patient interface device 18 (e.g., without limitation, a mask) via conduit 12.

Base unit 14 includes a heating control unit 20. First, second, and third resistive wires 22, 24, 26 extend along conduit 12. A thermistor 28 is disposed in conduit 12 to sense the temperature of airflow 16 through conduit 12. Heating control unit 20 includes a first voltage source 30, a second voltage source 32, a first switch 34, and a second switch 36. First voltage source 30 has a higher voltage than second voltage source 32. Voltage from first voltage source 30 is used to provide heating for conduit 12 via second and third resistive wires 24 and 26. Second voltage source 32 is used to provide a voltage across thermistor 28 to sense the temperature of airflow 16. A neutral reference point 38 (e.g., without limitation, a ground) is also provided in heating control unit 20.

First voltage source 30, first switch 34, second resistive wire 24, third resistive wire 26, and neutral reference point 38 are arranged in series. To provide heating of airflow 16, first switch 34 is closed by a processor 40 in heating control unit 20 which allows current to flow from first voltage source 30 to neutral reference point 38 via second and third resistive wires 24 and 26. The current passing through second and third resistive wires 24 and 26 heats second and third resistive wires 24 and 26 which heats airflow 16.

Second voltage source 32, second switch 36, a pull-up resistor 42, first resistive wire 22, thermistor 28, third resistive wire 26, and neutral reference point 38 are arranged in series. To sense temperature of airflow 16 via thermistor 28, second switch 36 is closed by processor 40 which allows current to flow through thermistor 28. Processor 40 is electrically connected to first resistive wire 22 to measure the output of thermistor 28 to determine the temperature of airflow 16.

The pressure support system 10 uses three resistive wires 22, 24, 26 that extend along conduit 12 to heat and measure a temperature of airflow 16. Each resistive wire adds to the cost and complexity of pressure support system 10.

SUMMARY OF THE INVENTION

There are strong cost, design and manufacturing simplicity benefits for CPAP and other respiratory devices to change the heated wire breathing circuit (HWC) from a 3-wire or 4-wire format (2 wire heating loop+thermistor wire(s)) to a 2-wire format. The benefits of the 2-wire format include improved flexibility of the HWC for better patient comfort, simplified tubing manufacturing and reduced cost, simplified connector interface to the respiratory device, etc. But there are technical challenges in providing both the heating function and proximal patient temperature measuring function when only 2 wires are utilized in said circuit. Embodiments of the present invention provides a closed loop temperature control with only a 2-wire circuit while still providing proximal patient temperature measurement and a means for tube type identification.

As one aspect of the invention, a conduit for communicating a flow of breathing gas from a pressure generating device to the airway of a patient is provided. The conduit comprises: a first end structured to be coupled to the pressure generating device for receiving the flow of breathing gas; an opposite second end which is structured to be coupled to a patient interface device; an active control element positioned at or near the second end; a first heating wire connected between the active control element and a first connection terminal positioned at or about the first end; and a second heating wire connected between the active control element and a second connection terminal positioned at or about the first end, wherein each of the first and second connection terminals are structured to be connected to a tube power supply.

The active control element may comprise: a bootstrap power supply having an output; a switch connected between the first heating wire and the second heating wire; and a circuit connected between the output and the switch for controlling operation of the switch. The circuit may be structured to selectively operate the switch dependent on the temperature of a portion of the circuit. A frequency and a duty cycle of the selective operation of the switch may be dependent on the temperature of a portion of the circuit. The active control element may comprise: a bootstrap power supply having an output; a switch connected between the first heating wire and the second heating wire; and a microcontroller connected between the output and the switch, wherein the microcontroller is programmed to selectively operate the switch. The microcontroller may be programmed to selectively operate the switch dependent on the temperature of the conduit. A frequency and a duty cycle of the operation of the switch may be dependent on the temperature of the conduit. The microcontroller may be programmed to selectively operate the switch dependent on an identifier of the conduit programmed in the microcontroller. The microcontroller may be programmed to selectively operate the switch dependent on a sensed property of the gas flow other than temperature. The conduit may further comprise a reference wire which is connected between the active control element and the first connection terminal; wherein the active control element comprises: a power supply connected between the reference wire and a connection point between the first heating wire and the second heating wire; a microcontroller connected to an output of the power supply; and a switching element connected between the first heating wire and the second heating wire, wherein the microcontroller is programmed to selectively operate the switch. The microcontroller may be programmed to selectively operate the switch dependent on the temperature of the conduit.

As another aspect of the present invention, an airway pressure support system for delivering a flow of breathing gas to an airway of a patient is provided. The system comprises: a pressure generating device base unit structured to produce the flow of breathing gas, the pressure generating device having a power supply; a conduit having: a first end coupled to the base unit for receiving the flow of breathing gas; a second end opposite the first end, the conduit being structured to convey the flow of breathing gas from the first end to the second end; an active control element positioned at or near the second end; a first heating wire connected between the active control element and a first connection terminal positioned at or about the first end, the first connection terminal being selectively connected to the power supply; and a second heating wire connected between the active control element and a second connection terminal positioned at or about the first end, the second connection terminal being selectively connected to the power supply; and a patient interface device coupled to the second end of the conduit, the patient interface device being structured to sealing engage about the airway of the patient and to convey the flow of breathing gas from the second end of the conduit to the airway of the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
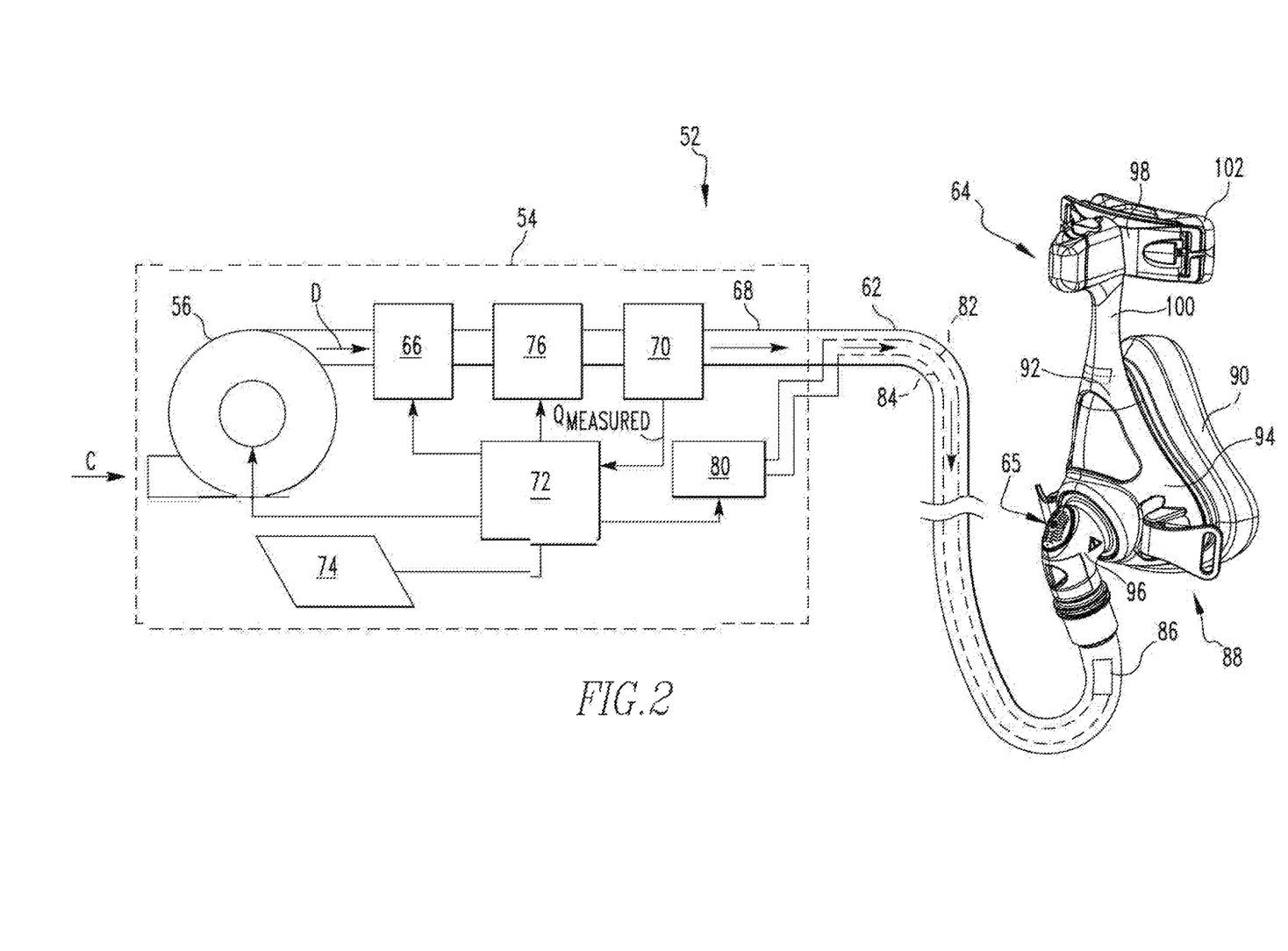
FIG. 2 is a schematic diagram of an airway pressure support system according to one example embodiment of the present invention.

FIG. 2 is a schematic diagram showing an airway pressure support system 52 according to one particular, non-limiting exemplary embodiment. Airway pressure support system 52 includes a pressure generating device base unit 54 which houses a gas flow generator 56, such as a blower used in a conventional CPAP or bi-level pressure support device. Gas flow generator 56 receives breathing gas, generally indicated by arrow C, from the ambient atmosphere and generates a flow of breathing gas therefrom for delivery to an airway of a patient at relatively higher and lower pressures, i.e., generally equal to or above ambient atmospheric pressure. In the exemplary embodiment, gas flow generator 60 is capable of providing a flow of breathing gas ranging in pressure from 3-30 cmH2O. The pressurized flow of breathing gas from gas flow generator 60, generally indicated by arrow D, is delivered via a delivery conduit 62 to a patient interface device 64 of any known construction, which is typically worn by or otherwise attached to a patient to communicate the flow of breathing gas to the airway of the patient. Delivery conduit 62 and patient interface device 64 are typically collectively referred to as a patient circuit.

Pressure support system 52 shown in FIG. 2 is what is known as a single-limb system, meaning that the patient circuit includes only delivery conduit 62 connecting the patient to base unit 54. As such, an exhaust vent 65 is provided on or near patient interface device 64 for venting exhaled gases from the system. It should be noted that the exhaust vent can be provided at other locations. It should also be understood that the exhaust vent can have a wide variety of configurations depending on the desired manner in which gas is to be vented from pressure support system 52.

The present invention also contemplates that pressure support system 52 can be a two-limb system, having a delivery conduit and an exhaust conduit connected to a patient. In a two-limb system (also referred to as a dual-limb system), the exhaust conduit carries exhaust gas from the patient and includes an exhaust valve at the end distal from the patient. The exhaust valve in such an embodiment is typically actively controlled to maintain a desired level or pressure in the system, which is commonly known as positive end expiratory pressure (PEEP).

In the illustrated embodiment, pressure support system 52 includes a pressure controller in the form of a valve 66 provided in an internal delivery conduit 68 provided in pressure generating device base unit 54 of pressure support system 52. Valve 66 controls the pressure of the flow of breathing gas from gas flow generator 56 that is delivered to the patient via patient interface device 64. For present purposes, gas flow generator 56 and valve 66 are collectively referred to as a pressure generating system because they act in concert to control the pressure and/or flow of gas delivered to a patient. However, it should be apparent that other techniques for controlling the pressure of the gas delivered to a patient, such as varying the blower speed of gas flow generator 56, either alone or in combination with a pressure control valve, are contemplated by the present invention. Thus, valve 66 is optional depending on the technique used to control the pressure of the flow of breathing gas delivered to a patient. If valve 66 is eliminated, the pressure generating system corresponds to gas flow generator 56 alone, and the pressure of gas in the patient circuit is controlled, for example, by controlling the motor speed of gas flow generator 56.

Pressure support system 52 further includes a flow sensor 70 that measures the flow of the breathing gas within internal delivery conduit 68 and delivery conduit 62. In the particular embodiment shown in FIG. 2, flow sensor 20 is interposed in line with conduits 68 and 62, most preferably downstream of valve 66. Flow sensor 70 generates a flow signal, $Q_{MEASURED}$, that is provided to a controller 72 and is used by controller 72 to determine the flow of gas at a patient ($Q_{PATIENT}$).

Techniques for calculating $Q_{PATIENT}$ based on $Q_{MEASURED}$ are well known, and take into consideration the pressure drop of the patient circuit, known leaks from the system, i.e., the intentional exhausting of gas from the circuit as described herein, and unknown (unintentional) leaks from the system, such as leaks at the mask/patient interface. The present invention contemplates using any known or hereafter developed technique for calculating total leak flow $Q_{LEAK}$, and using this determination in calculating $Q_{PATIENT}$ based on $Q_{MEASURED}$ (and for other purposes as described elsewhere herein). Examples of such techniques are taught by U.S. Pat. Nos. 5,148,802; 5,313,937; 5,433,193; 5,632, 269; 5,803,065; 6,029,664; 6,539,940; 6,626,175; and 7,011, 091, the contents of each of which are incorporated by reference into the present invention.

Of course, other techniques for measuring the respiratory flow of a patient are contemplated by the present invention, such as, without limitation, measuring the flow directly at the patient or at other locations along delivery conduit 62, measuring patient flow based on the operation of gas flow generator 56, and measuring patient flow using a flow sensor upstream of valve 66.

Controller 72 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 52.

An input/output device 74 is provided for setting various parameters used by airway pressure support system 52, as well as for displaying and outputting information and data to a user, such as a clinician or caregiver.

Furthermore, in the illustrated embodiment, pressure support system 52 also includes a humidifier 76 provided in base unit 54 of pressure support system 52. Alternatively, humidifier 76 may be separate from, and located external to, base unit 54. Humidifier 76 is controlled by controller 72. Humidifier 76 further improves comfort by providing moisture in the supplied gas. In the exemplary embodiment, humidifier 76 is a passover type humidifier. U.S. Patent Application Publication No. 2007/0169776, incorporated herein by reference in its entirety, discloses an exemplary humidifier device suitable for use in the present invention. Humidifier devices having alternative designs, such as a non-passover type humidifier that employs nebulization, atomization, vaporization or a combination thereof, may also be used.

Continuing to refer to FIG. 2, pressure support system 52 includes a tube power supply 80 included in pressure support system base unit 4 which may be controlled by controller 72. Conduit 62 includes first and second resistive wires 82, 84 (shown in hidden line, also referred to herein as first and second heating wires 82, 84) that extend along conduit 62. An active control element 86 is also included in conduit 62, the contents of which are discussed further below. First and second heating wires 82 and 84 are electrically coupled between tube power supply 80 and active control element 86. Tube power supply 80 is structured to provide power to first and second heater wires 82 and 84 to heat airflow in conduit 62.

In the exemplary embodiment, patient interface device 64 includes a patient sealing assembly 88, which in the illustrated embodiment is a full face mask (i.e., covers both the nose and mount of a patient). However, other types of patient sealing assemblies, such as, without limitation, a nasal mask, a nasal cushion, or a nasal/oral mask, which facilitate the delivery of the flow of breathing gas to the airway of a patient may be substituted for patient sealing assembly 88 while remaining within the scope of the present invention. Patient sealing assembly 88 includes a cushion 90 coupled to a frame member 92. In the illustrated embodiment, cushion 90 is defined from a unitary piece of soft, flexible, cushiony, elastomeric material, such as, without limitation, silicone, an appropriately soft thermoplastic elastomer, a closed cell foam, or any combination of such materials. Also in the illustrated embodiment, frame member 92 is made of a rigid or semi-rigid material, such as, without limitation, an injection molded thermoplastic or silicone, and includes a faceplate portion 94 to which cushion 90 is fluidly attached. A fluid coupling conduit 96 having exhaust vent 65 is coupled to an opening in faceplate portion 94 to allow the flow of breathing gas from pressure generating device base unit 54 to be communicated to an interior space defined by cushion 90, and then to the airway of a patient.

Frame member 92 also includes a forehead support 98 that is coupled to the faceplate portion 94 by a connecting member 100. A forehead cushion 102 is coupled to the rear of forehead support 98. In the exemplary embodiment, forehead cushion 102 is made of a material that is similar to the material of cushion 90.

Patient interface device 64 also includes a headgear component (not shown) for securing patient interface device 64 to the head of a patient. Any suitable headgear arrangement may be employed without varying from the scope of the present invention.

In the illustrated, non-limiting exemplary embodiment of the present invention, airway pressure support system 2 essentially functions as a CPAP pressure support system, and, therefore, includes all of the capabilities necessary in such systems in order to provide appropriate CPAP pressure levels to a patient. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 3A:
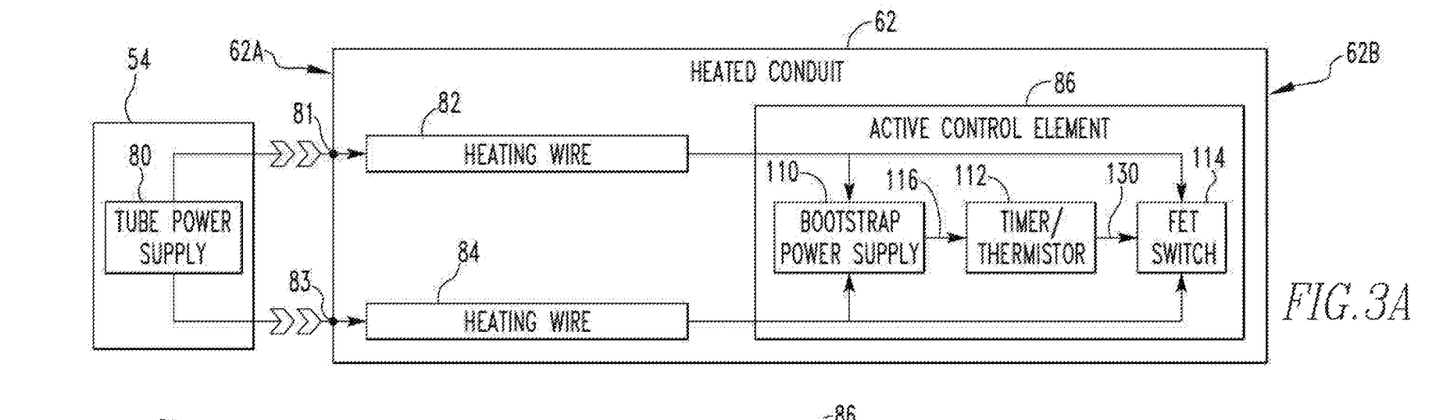
FIG. 3A is a simplified schematic diagram of an arrangement including a heated tube according to one example embodiment of the present invention.
Figure 3B:
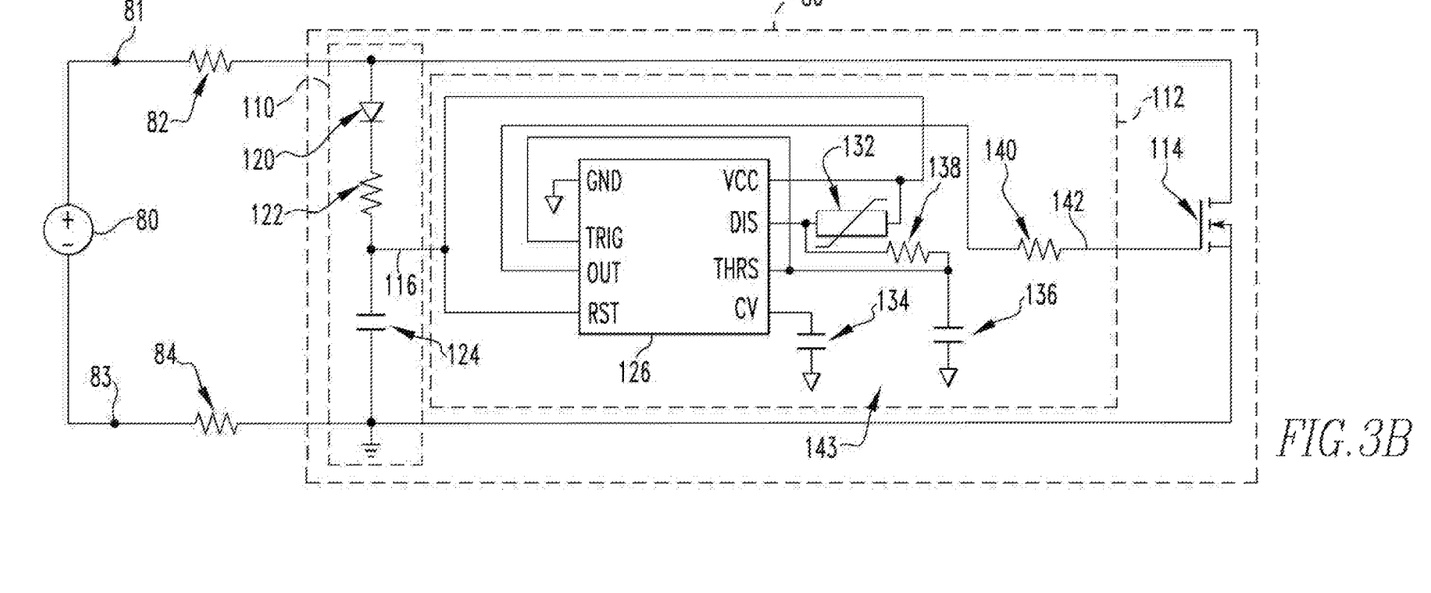
FIG. 3B is a schematic diagram of an implementation of the arrangement of FIG. 3A according to one example embodiment of the present invention.

FIG. 3A is a simplified schematic diagram of heated conduit 62 according to one example embodiment of the present invention shown connected to tube power supply 80 of base unit 54, and FIG. 3B is a more detailed wiring schematic of an example embodiment of the arrangement of FIG. 3A. Referring to FIG. 3A, conduit 62 includes a first end 62A structured to be coupled to base unit 54 in order to receive the flow of breathing gas produced by gas flow generator 56, and an opposite second end 62B which is structured to be coupled to patient interface device 64. Conduit 62 is structured to convey the flow of breathing gas from first end 62A to second end 62B which is then conveyed to the airway of a patient via patient interface device 64. As previously discussed, heated conduit 62 includes first and second heating wires 82 and 84, which each extend from a respective connection terminal 81, 83 positioned at or about first end 62A, along conduit 62, to active control element 86, which is preferably disposed generally at or about second end 62B of conduit 62. Each of first and second heating wires 82 and 84 are electrically connected, via a respective one of connection terminals 81 or 83, between tube power supply 80 and active control element 86.

Continuing to refer to FIG. 3A, active control element 86 includes a power supply, such as bootstrap power supply 110, a timer/thermistor circuit 112, and a switching element, such as field-effect transistor (FET) switch 114. Bootstrap power supply 110 is connected between first heating wire 82 and second heating wire 84. In the example embodiment illustrated in FIG. 3B, bootstrap power supply 110 includes a diode 120, a resistor 122 and a capacitor 124 connected in a series arrangement between first heating wire 82 and second heating wire 84. An output 116 (i.e., an unregulated power supply) from bootstrap power supply 110 is connected to timer/thermistor circuit 112, providing power thereto.

Continuing to refer to FIG. 3B, timer/thermistor circuit 112 includes a timer arrangement 126 receiving power from output 116 from bootstrap power supply 110, as well as a thermistor 132, capacitors 134 and 136, and resistors 138 and 140. An output 142 from timer/thermistor circuit 112 is connected to FET switch 114 so as to control the positioning (i.e., open or closed) of FET switch 114. FET switch 114 is connected between first and second heating wires 82 and 84 (in a parallel arrangement with bootstrap power supply 110) such that when power is applied to heating wires 82 and 84 (e.g., via tube power supply 80) and FET switch 114 is in a closed position, current flows though heating wires 82 and 84, thus heating conduit 62, and when FET switch is in an open position, current does not flow through heating wires 82 and 84 (except for the very short time in which bootstrap power supply 110 takes to charge) and thus no heat is produced.

In operation, bootstrap power supply 110 is initially charged when power is applied to first and second heating wires 82 and 84 by tube power supply 80 (e.g., when conduit 62 is first connected or after conduit 62 is connected and tube power supply 80 is turned on. Such charging occurs nominally in less than 1 ms for example if a 2 uF capacitor 124 is used. Once charged, timer 126 powers up and begins running, nominally as a continuous oscillator. The frequency and duty-cycle of the oscillator are a function of a timing resistor and capacitor network 143 (consisting of capacitors 134 and 136, and thermistor 132, and resistors 138 and 140). Thermistor 138 mainly controls timing, while capacitor 136 and resistor 138 are both related to timing and dutycycle. Capacitor 134 may be utilized in setting a particular threshold. Therefore the frequency of the oscillator will be a function of the temperature of thermistor 138, and therefore a function of the temperature of conduit 62.

As output 130 of circuit 112 controls FET switch 114, as the oscillator cycles, FET switch 114 is alternatively turned on and off. When FET switch 114 is turned on, active control element 86 is completely powered by bootstrap power supply 110. Therefore the oscillator must periodically turn off FET switch 114 to allow bootstrap power supply 110 to recharge.

The heating function of conduit 62 is accomplished by tube power supply 80 charging bootstrap power supply 110, circuit 124 turning on FET switch 114 and periodically turning the FET switch off 114 briefly to recharge bootstrap power supply 110. The pulse train created in the current flow through first and second heating wires 82 and 84 by the opening and closing of FET switch 114 generates a corresponding conduit current pattern that is measured in tube power supply 80. From such measurement, the temperature of thermistor 138 in active control element 86, and hence the temperature of the flow of breathing gas passing through conduit 62 can thus generally be determined. From such determination tube power supply 80 can thus be regulated to obtain/maintain a desired temperature.

Furthermore, by selecting among multiple thermistors with differing nominal characteristics for use in circuit 112 which thus each would result in FET switch 114 being activated in a different frequency range, the particular thermistor employed in a particular conduit can be identified, and thus a particular tube identity can be distinguished.

Figure 4A:
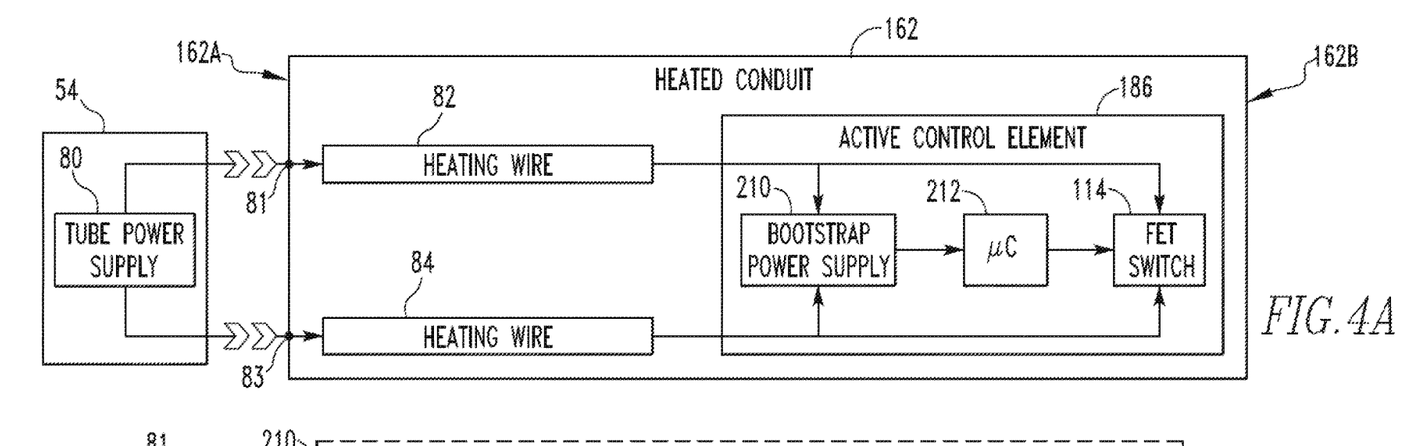
FIG. 4A is a simplified schematic diagram of an arrangement including a heated tube according to one example embodiment of the present invention.
Figure 4B:
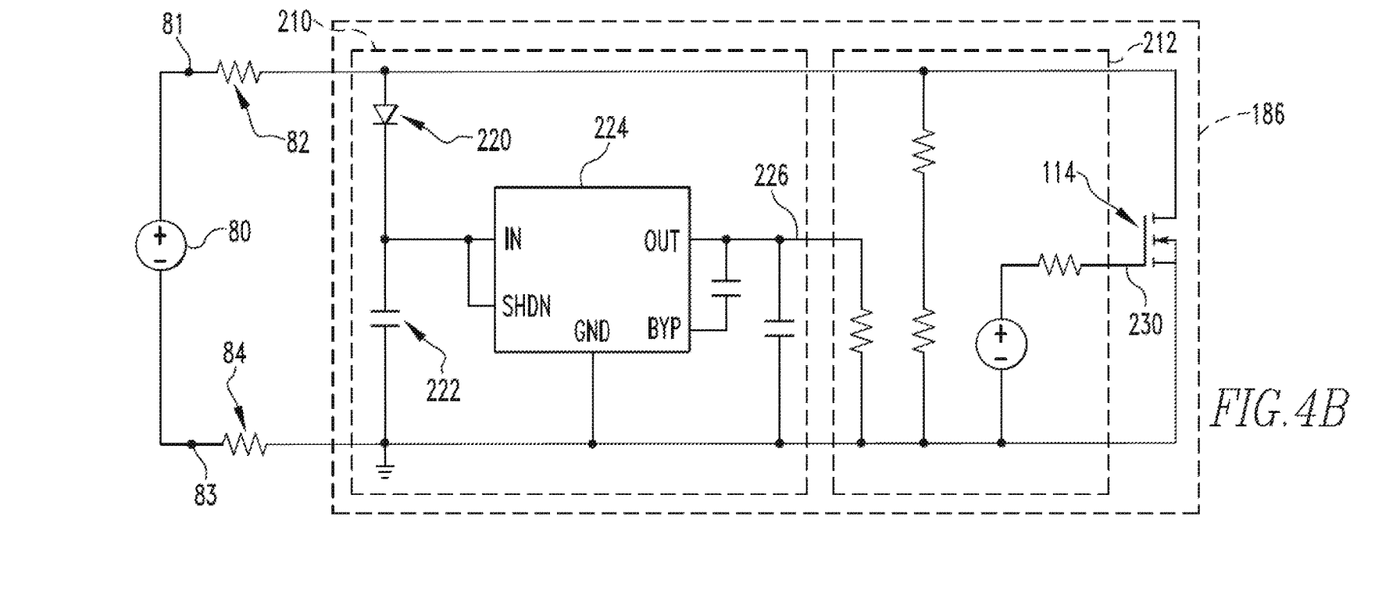
FIG. 4B is a schematic diagram of an implementation of the arrangement of FIG. 4A according to one example embodiment of the present invention.

FIG. 4A is a simplified schematic diagram of another heated conduit 162 according to another example embodiment of the present invention shown connected to tube power supply 80 of base unit 54, such as shown in FIG. 1. FIG. 4B is a more detailed wiring schematic of an example embodiment of the arrangement of FIG. 4A. Referring to FIG. 4A, conduit 162 includes a first end 162A structured to be coupled to base unit 54 in order to receive the flow of breathing gas produced by gas flow generator 56, and an opposite second end 162B which is structured to be coupled to patient interface device 64. Conduit 162 is structured to convey the flow of breathing gas from first end 162A to second end 162B which then is conveyed to the airway of a patient via patient interface device 64. Similar to conduit 62, previously discussed, heated conduit 162 includes first and second heating wires 82 and 84, which each extend from a respective connection terminal 81, 83 positioned at or about first end 162A, along conduit 162, to active control element 186, which is preferably disposed generally at or about second end 162B of conduit 162. Each of first and second heating wires 82 and 84 are electrically connected, via a respective one of connection terminals 81 or 83, between tube power supply 80 and active control element 186.

Active control element 186 includes a power supply, such as bootstrap power supply 210, a microcontroller 212, and a switching element, such as field-effect transistor (FET) switch 114. Bootstrap power supply 210 is connected between first heating wire 82 and second heating wire 84. In the example embodiment illustrated in FIG. 4B, bootstrap power supply 210 includes a diode 220 and a capacitor 222 connected in a series arrangement between first heating wire 82 and second heating wire 84. Power supply 210 further includes a voltage regulator 224 having an input connected between diode 220 and capacitor 222. An output 226 from power supply 210 is connected to microcontroller 212, providing power thereto. An output 230 from microcontroller 212 is connected to FET switch 114 so as to control the positioning (i.e., open or closed) of FET switch 114. FET switch 114 is connected between first and second heating wires 82 and 84 such that when power is applied to heating wires 82 and 84 (e.g., via tube power supply 80) and FET switch 114 is in a closed position, current flows though heating wires 82 and 84 thus heating conduit 162, and when FET switch 114 is in an open position, current does not flow through heating wires 82 and 84 and thus no heat is produced.

In operation, power supply 210 is initially charged when power is applied to first and second heating wires 82 and 84 by tube power supply 80 (e.g., when conduit 162 is first connected or after conduit 162 is connected and tube power supply 80 is turned on. Such charging occurs nominally in less than 1 ms for example if a 2 uF capacitor 222 is used. Once charged, microcontroller 212 can power up and perform measurements (e.g., conduit temperature via an embedded temperature sensor or other suitable means). Microcontroller 212 turns on FET switch 114 for heating. When FET switch 114 is engaged, active control element 186 is completely powered by power supply 210. Accordingly, microcontroller 212 must periodically turn off FET switch 114 to allow power supply 210 to recharge.

The heating function of conduit 162 is accomplished by tube power supply 80 charging power supply 210, microcontroller 212 turning on FET switch 114 and periodically turning the FET switch 114 off briefly to recharge power supply 210. The pulse train created in the current flow through first and second heating wires 82 and 84 by the opening and closing of FET switch 114 generates a corresponding conduit current pattern that is measured in tube power supply 80. As the timing of the pulse train is controlled by microcontroller 212, a modulation scheme to the timing of the pulse train can be imposed and information communicated to base unit 54 from microcontroller 212. Such information can include: tube identification (e.g., tube diameter), tube temperature, and/or other sensor information. Using such information communicated to base unit 54, tube power supply 80 can thus be regulated to obtain/maintain a desired temperature. Additionally, over temperature protection can be provided by the microcontroller 212 monitoring the temperature of conduit 162 and disabling FET switch 114 from closing if a temperature threshold is exceeded.

As an alternative to base unit controlling the temperature of conduit 162 via regulating tube power supply 80, microcontroller 212 may instead be used to generally control the heating function of conduit 162. As long as tube power supply 80 is providing power to first and second heating wires 82 and 84, microcontroller 212 can sense and control the temperature of conduit 162 by selectively opening and closing FET switch 114.

Figure 5A:
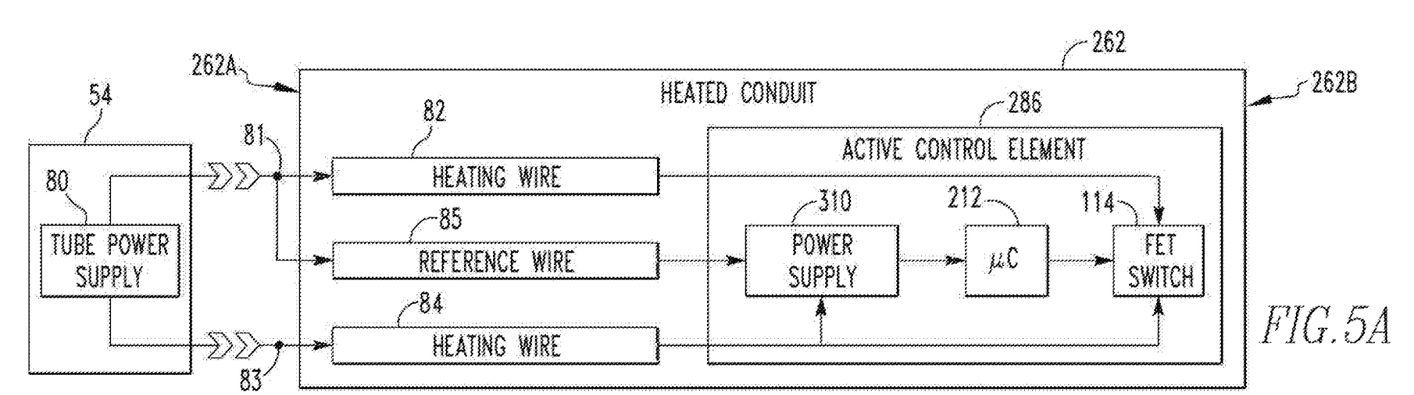
FIG. 5A is a simplified schematic diagram of an arrangement including a heated tube according to one example embodiment of the present invention.
Figure 5B:
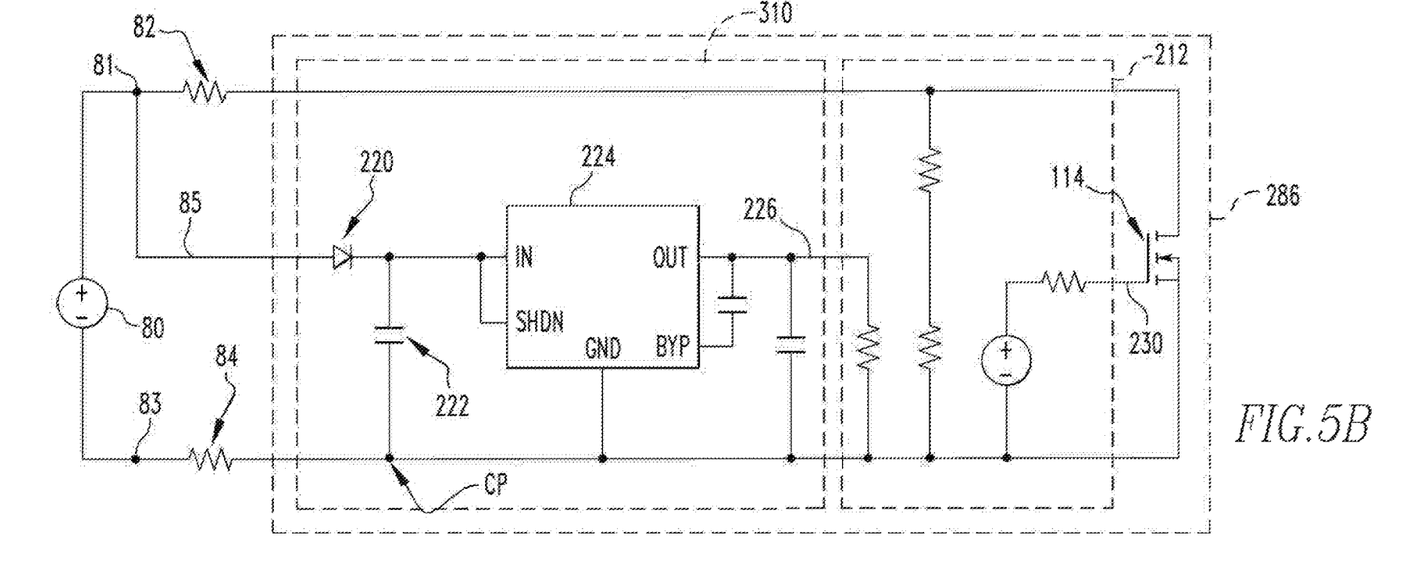
FIG. 5B is a schematic diagram of an implementation of the arrangement of FIG. 5A according to one example embodiment of the present invention.

FIG. 5A is a simplified schematic diagram of yet another heated conduit 262 according to yet another example embodiment of the present invention shown connected to tube power supply 80 of base unit 54, such as shown in FIG. 1. FIG. 5B is a more detailed wiring schematic of an example embodiment of the arrangement of FIG. 5A. Referring to FIG. 5A, conduit 262 includes a first end 262A structured to be coupled to base unit 54 in order to receive the flow of breathing gas produced by gas flow generator 56, and an opposite second end 262B which is structured to be coupled to patient interface device 64. Conduit 262 is structured to convey the flow of breathing gas from first end 262A to second end 262B which then is conveyed to the airway of a patient via patient interface device 64. Similar to conduits 62 and 162, previously discussed, heated conduit 262 includes first and second heating wires 82 and 84, which each extend from a respective connection terminal 81, 83 positioned at or about first end 262A, along conduit 262, to active control element 286, which is preferably disposed generally at or about second end 262B of conduit 162. Each of first and second heating wires 82 and 84 are electrically connected, via a respective one of connection terminals 81 or 83, between tube power supply 80 and active control element 286. Unlike conduits 62 and 162, conduit 262 further includes a reference wire 85 which is connected between connection terminal 81 and active control element 286.

Active control element 286 includes a power supply 310, a microcontroller 212, and a switching element, such as field-effect transistor (FET) switch 114. Power supply 310 is connected between connection terminal 81 and a connection point CP between first heating wire 82 and second heating wire 84. In the example embodiment illustrated in FIG. 5B, power supply 310 includes a diode 220 and a capacitor 222 connected in a series arrangement between connection terminal 81 and connection point CP. Power supply 310 further includes a voltage regulator 224 having an input connected between diode 220 and capacitor 222. An output 226 from power supply 210 is connected to microcontroller 212, providing power thereto. An output 230 from microcontroller 212 is connected to FET switch 114 so as to control the positioning (i.e., open or closed) of FET switch 114. FET switch 114 is connected between first and second heating wires 82 and 84 such that when power is applied to heating wires 82 and 84 (e.g., via tube power supply 80) and FET switch 114 is in a closed position, current flows though heating wires 82 and 84 thus heating conduit 262, and when FET switch 114 is in an open position, current does not flow through heating wires 82 and 84 and thus no heat is produced.

In operation, the arrangement of conduit 262 provides the same functionality as conduit 162 without the need for opening of FET switch 114 to charge power supply 310, as power supply 310 is powered directly by tube power supply 80.

Figure 6A:
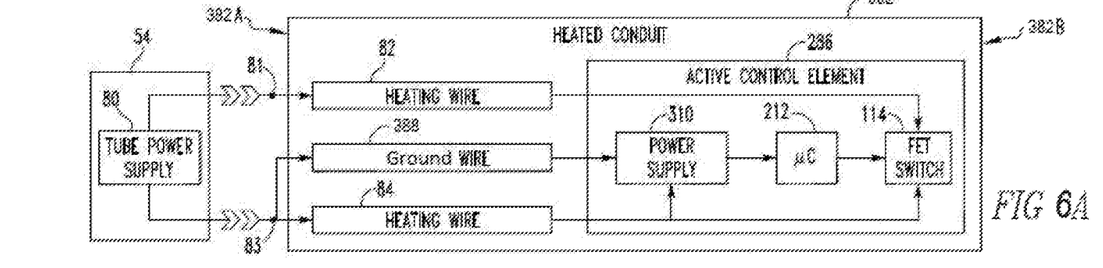
FIG. 6A is a simplified schematic diagram of an arrangement including a heated tube according to one example embodiment of the present invention.
Figure 6B:
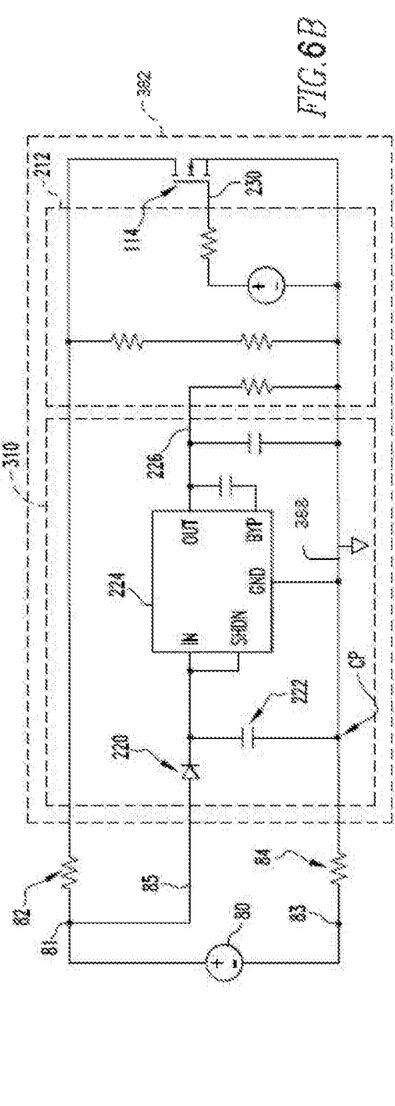
FIG. 6B is a schematic diagram of an implementation of the arrangement of FIG. 6A according to one example embodiment of the present invention.

FIG. 6A is a simplified schematic diagram of a still embodiment of a heated conduit 382 according to yet another example embodiment of the present invention shown connected to tube power supply 80 of base unit 54, such as shown in FIG. 1. FIG. 6B is a more detailed wiring schematic of an example embodiment of the arrangement of FIG. 6A. Referring to FIG. 6A, conduit 382 includes a first end 382A structured to be coupled to base unit 54 in order to receive the flow of breathing gas produced by gas flow generator 56, and an opposite second end 382B which is structured to be coupled to patient interface device 64.

In this embodiment, communication from base unit 54 to tube is accomplished by the base unit modulating the power delivery to the tube. Communication from tube-to-base unit is accomplished by the tube modulating the FET, which controls current flow through the heater wires, which is in turn measured by the CPAP. In this embodiment, a ground wire 388 is provided as a reference point for the FET.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A conduit for communicating a flow of breathing gas from a pressure generating device to the airway of a patient, the conduit comprising:

a first end structured to be coupled to the pressure generating device for receiving the flow of breathing gas;
an opposite second end structured to be coupled to a patient interface device;
an active control element positioned at or near the second end;
a first heating wire connected between the active control element and a first connection terminal positioned at or about the first end; and
a second heating wire connected between the active control element and a second connecting terminal positioned at or about the first end, wherein each of the first and second connection terminal are structured to be connected to a tube power supply,
wherein the active control element comprises:
a bootstrap power supply having an output;
a switch connected between the first heating wire and the second heating wire; and
a circuit connected between the output and the switch for controlling operation of the switch.

2. The conduit of claim 1, wherein the circuit is structured to selectively operate the switch dependent on the temperature of a portion of the circuit.

3. The conduit of claim 2, wherein a frequency and a duty cycle of the selective operation of the switch is dependent on the temperature of the portion of the circuit.

4. An airway pressure support system for delivering a flow of breathing gas to an airway of a patient, the system comprising:
a pressure generating device base unit structured to produce the flow of breathing gas, the pressure generating device base unit having a power supply;
the conduit of claim 1; and
a patient interface device coupled to the second end of the conduit, the patient interface device being structured to sealing engage about the airway of the patient and to convey the flow of breathing gas from the second end of the conduit to the airway of the patient.

5. A conduit for communicating a flow of breathing gas from a pressure generating device to the airway of a patient, the conduit comprising:
a first end structured to be coupled to the pressure generating device for receiving the flow of breathing gas;
an opposite second end structured to be coupled to a patient interface device;
an active control element positioned at or near the second end;
a first heating wire connected between the active control element and a first connection terminal positioned at or about the first end; and
a second heating wire connected between the active control element and a second connecting terminal positioned at or about the first end, wherein each of the first and second connection terminal are structured to be connected to a tube power supply,
wherein the active control element comprises:
a bootstrap power supply having an output;
a switch connected between the first heating wire and the second heating wire; and
a microcontroller connected between the output and the switch, wherein the microcontroller is programmed to selectively operate the switch.

6. The conduit of claim 5, wherein the microcontroller is programmed to selectively operate the switch dependent on the temperature of the conduit.

7. The conduit of claim 6, wherein a frequency and a duty cycle of the operation of the switch is dependent on the temperature of the conduit.

8. The conduit of claim 5, wherein the microcontroller is programmed to selectively operate the switch dependent on an identifier of the conduit programmed in the microcontroller.

9. The conduit of claim 5, wherein the microcontroller is programmed to selectively operate the switch dependent on a sensed property of the gas flow other than temperature.

10. An airway pressure support system for delivering a flow of breathing gas to an airway of a patient, the system comprising:
a pressure generating device base unit structured to produce the flow of breathing gas, the pressure generating device base unit having a power supply;
the conduit of claim 5; and
a patient interface device coupled to the second end of the conduit, the patient interface device being structured to sealing engage about the airway of the patient and to convey the flow of breathing gas from the second end of the conduit to the airway of the patient.

11. A conduit for communicating a flow of breathing gas from a pressure generating device to the airway of a patient, the conduit comprising:
a first end structured to be coupled to the pressure generating device for receiving the flow of breathing gas;
an opposite second end structured to be coupled to a patient interface device;
an active control element positioned at or near the second end;
a first heating wire connected between the active control element and a first connection terminal positioned at or about the first end; and
a second heating wire connected between the active control element and a second connecting terminal positioned at or about the first end, wherein each of the first and second connection terminal are structured to be connected to a tube power supply,
a reference wire connected between the active control element and the first connection terminal,
wherein the active control element comprises:
a power supply connected between the reference wire and a connection point between the first heating wire and the second heating wire;
a microcontroller connected to an output of the power supply; and
a switching element connected between the first heating wire and the second heating wire, wherein the microcontroller is programmed to selectively operate the switching element.

12. The conduit of claim 11, wherein the microcontroller is programmed to selectively operate the switch dependent on the temperature of the conduit.

13. The conduit of claim 12, wherein a frequency and a duty cycle of the operation of the switch is dependent on the temperature of the conduit.

14. The conduit of claim 11, wherein the microcontroller is programmed to selectively operate the switch dependent on an identifier of the conduit programmed in the microcontroller.

15. The conduit of claim 11, wherein the microcontroller is programmed to selectively operate the switch dependent on a sensed property of the gas flow other than temperature.

16. An airway pressure support system for delivering a flow of breathing gas to an airway of a patient, the system comprising:
- a pressure generating device base unit structured to produce the flow of breathing gas, the pressure generating device base unit having a power supply;
- the conduit of claim 11; and
- a patient interface device coupled to the second end of the conduit, the patient interface device being structured to sealing engage about the airway of the patient and to convey the flow of breathing gas from the second end of the conduit to the airway of the patient.

* * * * *